US005763385A

United States Patent [19]

Bott et al.

[11] Patent Number: 5,763,385

[45] Date of Patent: Jun. 9, 1998

[54] MODIFIED α-AMYLASES HAVING ALTERED CALCIUM BINDING PROPERTIES

[75] Inventors: Richard R. Bott, Burlingame; Andrew Shaw, San Francisco, both of Calif.

[73] Assignee: Genencor International, Inc., Rochester, N.Y.

[21] Appl. No.: 645,971

[22] Filed: May 14, 1996

[51] Int. Cl.[6] .............................. C11D 7/42; C12N 9/26; C12N 9/28; C12N 15/00

[52] U.S. Cl. .......................... 510/392; 435/201; 435/202; 435/172.3; 435/836

[58] Field of Search .................................... 435/201, 202, 435/172.3, 836; 252/132; 510/392

[56] References Cited

U.S. PATENT DOCUMENTS 5,260,207 11/1993 Pantoliano et al. ..................... 435/221

FOREIGN PATENT DOCUMENTS

94/18314 8/1994 WIPO .

95/35382 12/1995 WIPO .

OTHER PUBLICATIONS

Boel et al., "Calcium Binding in α–Amylases: An X–ray Diffraction Study at 2.1–A Resolution of Two Enzymes from Aspergillus," *Biochemistry* (1990) 29:6244–6249.

Declerck, et al., "Hyperthermostable mutants of *Bacillus licheniformis* α–amylase: multiple amino acid replacements and molecular modelling," *Protein Engineering*, (1995) 8(10):1029–1037.

Holm et al., "Random mutagenesis used to probe the structure and function of *Bacillus stearothermophilus* alpha–amylase," *Protein Engineering*, (1990) 3(3):181–191.

Mosimann et al. "A Critical Assessment of Comparative Molecular Modeling of Tertiary Structures of Proteins," *Prot* (1995) 23:301–317.

Moult et al., "A Large–Scale Experiment to Assess Protein Structure Prediction Methods," *Prot* (1995) 23:ii–iv.

Samudrala et al., "Confronting the Problem of Interconnected Structural Changes in the Comparative Modeling of Proteins," *Prot* (1995) 23:327–336.

Suzuki et al., "Crystallization and Preliminary Crystallographic Study of Bacterial α–Amylases," *J. Biochem* (1990) 108:379–381.

Svensson, "Protein engineering in the α–amylase family: catalytic mechanism, substrate specificity, and stability," *Plant Mol Biol* (1994) 25:141–157.

Takase et al., "Site–directed mutagenesis of active site residues in *Bacillus subtilis* α–amylase," *Biochimica et Biophysica Acta*, (1992) 1120:281–288.

Vihinen et al., "Site–Directed Mutagenesis of a Thermostable α–Amylase from *Bacillus stearothermophilus*: Putative Role of Three Conserved Residues," *J. Biochem.* (1990) 107:267–272.

Machius et al. (1995) J. Mol. Biol. 246, 545–559.

*Primary Examiner*—Robert A. Wax

*Assistant Examiner*—Elizabeth Slobodyansky

*Attorney, Agent, or Firm*—Christopher L. Stone

[57] ABSTRACT

Novel α-amylase enzymes are disclosed in which a new calcium binding site is modified by chemically or genetically altering residues associated with that calcium binding site. The novel α-amylases have altered performance characteristics, such as low pH starch hydrolysis performance, stability and activity profiles.

28 Claims, 8 Drawing Sheets

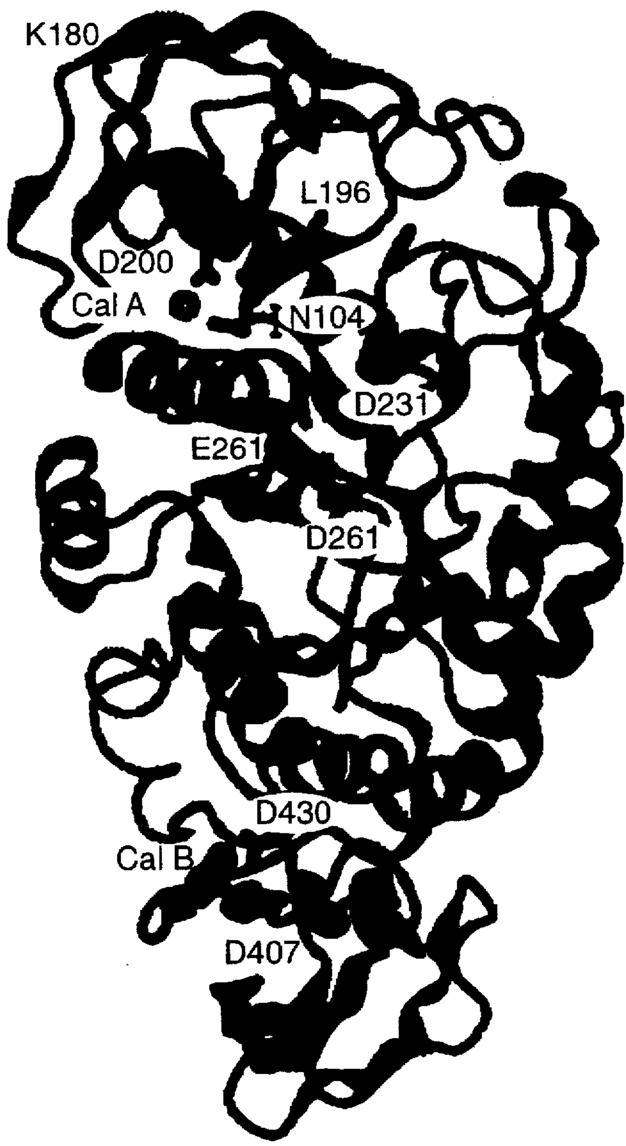
FIG._1

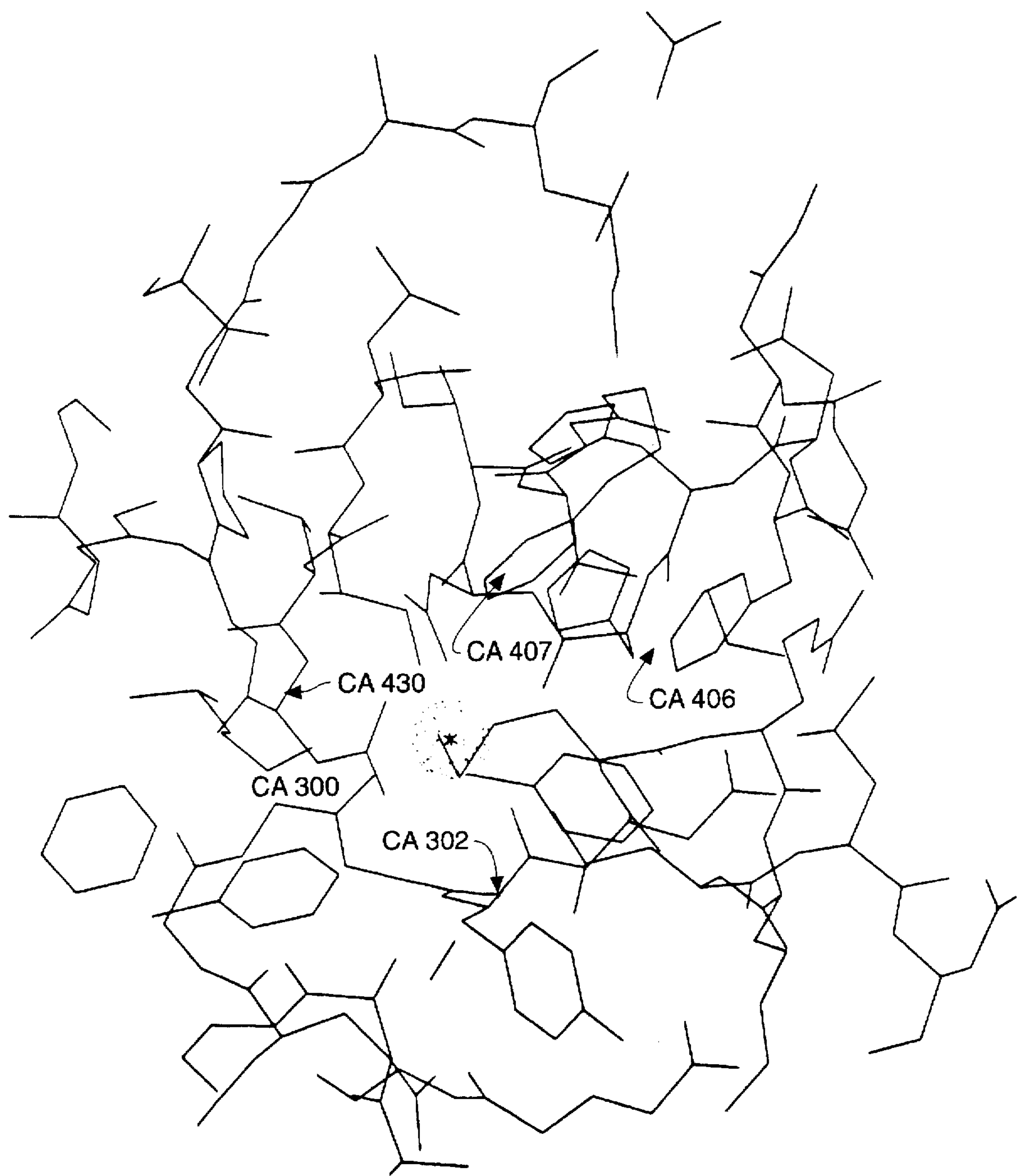
FIG._2

```
        10                                      30                                      50
AGCTTGAAGAAGTGAAGAAGCAGAGAGGCTATTGAATAAATGAGTAGAAAGCGCCATATC

        70                                      90                                     110
GGCGCTTTTCTTTTGGAAGAAAATATAGGGAAAATGGTACTTGTTAAAAATTCGGAATAT

       130                                     150                                     170
TTATACAACATCATATGTTTCACATTGAAAGGGGAGGAGAATCATGAAACAACAAAAACG
                                             M  K  Q  Q  K  R

       190                                     210                                     230
GCTTTACGCCCGATTGCTGACGCTGTTATTTGCGCTCATCTTCTTGCTGCCTCATTCTGC
 L  Y  A  R  L  L  T  L  L  F  A  L  I  F  L  L  P  H  S  A

       250                                     270                                     290
AGCAGCGGCGGCAAATCTTAATGGGACGCTGATGCAGTATTTTGAATGGTACATGCCCAA
 A  A  A  A  N  L  N  G  T  L  M  Q  Y  F  E  W  Y  M  P  N

       310                                     330                                     350
TGACGGCCAACATTGGAAGCGTTTGCAAAACGACTCGGCATATTTGGCTGAACACGGTAT
 D  G  Q  H  W  K  R  L  Q  N  D  S  A  Y  L  A  E  H  G  I

       370                                     390                                     410
TACTGCCGTCTGGATTCCCCCGGCATATAAGGGAACGAGCCAAGCGGATGTGGGCTACGG
 T  A  V  W  I  P  P  A  Y  K  G  T  S  Q  A  D  V  G  Y  G

       430                                     450                                     470
TGCTTACGACCTTTATGATTTAGGGGAGTTTCATCAAAAAGGGACGGTTCGGACAAAGTA
 A  Y  D  L  Y  D  L  G  E  F  H  Q  K  G  T  V  R  T  K  Y

       490                                     510                                     530
CGGCACAAAAGGAGAGCTGCAATCTGCGATCAAAAGTCTTCATTCCCGCGACATTAACGT
 G  T  K  G  E  L  Q  S  A  I  K  S  L  H  S  R  D  I  N  V

       550                                     570                                     590
TTACGGGGATGTGGTCATCAACCACAAAGGCGGCGCTGATGCGACCGAAGATGTAACCGC
 Y  G  D  V  V  I  N  H  K  G  G  A  D  A  T  E  D  V  T  A

       610                                     630                                     650
GGTTGAAGTCGATCCCGCTGACCGCAACCGCGTAATTTCAGGAGAACACCTAATTAAAGC
 V  E  V  D  P  A  D  R  N  R  V  I  S  G  E  H  L  I  K  A

       670                                     690                                     710
CTGGACACATTTTCATTTTCCGGGGCGCGGCAGCACATACAGCGATTTTAAATGGCATTG
 W  T  H  F  H  F  P  G  R  G  S  T  Y  S  D  F  K  W  H  W

       730                                     750                                     770
GTACCATTTTGACGGAACCGATTGGGACGAGTCCCGAAAGCTGAACCGCATCTATAAGTT
 Y  H  F  D  G  T  D  W  D  E  S  R  K  L  N  R  I  Y  K  F

       790                                     810                                     830
TCAAGGAAAGGCTTGGGATTGGGAAGTTTCCAATGAAAACGGCAACTATGATTATTTGAT
 Q  G  K  A  W  D  W  E  V  S  N  E  N  G  N  Y  D  Y  L  M
```

FIG._3A

```
     850                    870                     890
GTATGCCGACATCGATTATGACCATCCTGATGTCGCAGCAGAAATTAAGAGATGGGGCAC
 Y  A  D  I  D  Y  D  H  P  D  V  A  A  E  I  K  R  W  G  T
     910                    930                     950
TTGGTATGCCAATGAACTGCAATTGGACGGTTTCCGTCTTGATGCTGTCAAACACATTAA
 W  Y  A  N  E  L  Q  L  D  G  F  R  L  D  A  V  K  H  I  K
     970                    990                    1010
ATTTTCTTTTTTGCGGGATTGGGTTAATCATGTCAGGGAAAAAACGGGGAAGGAAATGTT
 F  S  F  L  R  D  W  V  N  H  V  R  E  K  T  G  K  E  M  F
    1030                   1050                    1070
TACGGTAGCTGAATATTGGCAGAATGACTTGGGCGCGCTGGAAAACTATTTGAACAAAAC
 T  V  A  E  Y  W  Q  N  D  L  G  A  L  E  N  Y  L  N  K  T
    1090                   1110                    1130
AAATTTTAATCATTCAGTGTTTGACGTGCCGCTTCATTATCAGTTCCATGCTGCATCGAC
 N  F  N  H  S  V  F  D  V  P  L  H  Y  Q  F  H  A  A  S  T
    1150                   1170                    1190
ACAGGGAGGCGGCTATGATATGAGGAAATTGCTGAACGGTACGGTCGTTTCCAAGCATCC
 Q  G  G  G  Y  D  M  R  K  L  L  N  G  T  V  V  S  K  H  P
    1210                   1230                    1250
GTTGAAATCGGTTACATTTGTCGATAACCATGATACACAGCCGGGGCAATCGCTTGAGTC
 L  K  S  V  T  F  V  D  N  H  D  T  Q  P  G  Q  S  L  E  S
    1270                   1290                    1310
GACTGTCCAAACATGGTTTAAGCCGCTTGCTTACGCTTTTATTCTCACAAGGGAATCTGG
 T  V  Q  T  W  F  K  P  L  A  Y  A  F  I  L  T  R  E  S  G
    1330                   1350                    1370
ATACCCTCAGGTTTTCTACGGGGATATGTACGGGACGAAAGGAGACTCCCAGCGCGAAAT
 Y  P  Q  V  F  Y  G  D  M  Y  G  T  K  G  D  S  Q  R  E  I
    1390                   1410                    1430
TCCTGCCTTGAAACACAAAATTGAACCGATCTTAAAAGCGAGAAAACAGTATGCGTACGG
 P  A  L  K  H  K  I  E  P  I  L  K  A  R  K  Q  Y  A  Y  G
    1450                   1470                    1490
AGCACAGCATGATTATTTCGACCACCATGACATTGTCGGCTGGACAAGGGAAGGCGACAG
 A  Q  H  D  Y  F  D  H  H  D  I  V  G  W  T  R  E  G  D  S
    1510                   1530                    1550
CTCGGTTGCAAATTCAGGTTTGGCGGCATTAATAACAGACGGACCCGGTGGGGCAAAGCG
 S  V  A  N  S  G  L  A  A  L  I  T  D  G  P  G  G  A  K  R
    1570                   1590                    1610
AATGTATGTCGGCCGGCAAAACGCCGGTGAGACATGGCATGACATTACCGGAAACCGTTC
 M  Y  V  G  R  Q  N  A  G  E  T  W  H  D  I  T  G  N  R  S
    1630                   1650                    1670
GGAGCCGGTTGTCATCAATTCGGAAGGCTGGGGAGAGTTTCACGTAAACGGCGGGTCGGT
 E  P  V  V  I  N  S  E  G  W  G  E  F  H  V  N  G  G  S  V
```

FIG._3B

```
     1690                        1710                        1730
TTCAATTTATGTTCAAAGATAGAAGAGCAGAGAGGACGGATTTCCTGAAGGAAATCCGTT
 S   I   Y   V   Q   R   *

     1750                        1770                        1790
TTTTTATTTTGCCCGTCTTATAAATTTCTTTGATTACATTTTATAATTAATTTTAACAAA

     1810                        1830                        1850
GTGTCATCAGCCCTCAGGAAGGACTTGCTGACAGTTTGAATCGCATAGGTAAGGCGGGGA

     1870                        1890                        1910
TGAAATGGCAACGTTATCTGATGTAGCAAAGAAAGCAAATGTGTCGAAAATGACGGTATC

     1930                        1950
GCGGGTGATCAATCATCCTGAGACTGTGACGGATGAATTGAAAAAGCT
```

FIG._3C

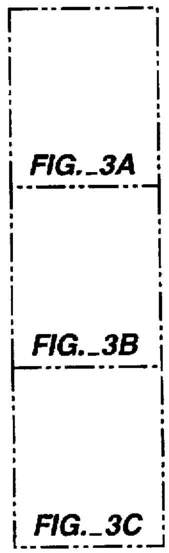

FIG._3

```
         10                                 30                             50
ANLNGTLMQYFEWYMPNDGQHWKRLQNDSAYLAEHGITAVWIPPAYKGTSQADVGYGAYD

         70                                 90                             110
LYDLGEFHQKGTVRTKYGTKGELQSAIKSLHSRDINVYGDVVINHKGGADATEDVTAVEV

         130                                150                            170
DPADRNRVISGEHLIKAWTHFHFPGRGSTYSDFKWHWYHFDGTDWDESRKLNRIYKFQGK

         190                                210                            230
AWDWEVSNENGNYDYLMYADIDYDHPDVAAEIKRWGTWYANELQLDGFRLDAVKHIKFSF

         250                                270                            290
LRDWVNHVREKTGKEMFTVAEYWQNDLGALENYLNKTNFNHSVFDVPLHYQFHAASTQGG

         310                                330                            350
GYDMRKLLNGTVVSKHPLKSVTFVDNHDTQPGQSLESTVQTWFKPLAYAFILTRESGYPQ

         370                                390                            410
VFYGDMYGTKGDSQREIPALKHKIEPILKARKQYAYGAQHDYFDHHDIVGWTREGDSSVA

         430                                450                            470
NSGLAALITDGPGGAKRMYVGRQNAGETWHDITGNRSEPVVINSEGWGEFHVNGGSVSIY

VQR
```

*FIG._4*

Am-Lich = *B.Licheniformis* Am-Amylo = *B.amyloliquefaciens* Am-Stearo = *B.stearothermophilus*

```
                                                                      1               19
            1                                                                         60
Am-Lich     ..............MKQQ KRLYARLLTL LFALIFLLPH ..............SAAA AANLNGTLMQ YFEWYMPNDG
Am-Amylo    MRGRGNMIQK RKRTVSFRLV LMCTLLFVSL ................PITK TSAVNGTLMQ YFEWYTPNDG
Am-Stearo   ................VLTF HRIIRKGWMF LLAFLLTASL FCPTGRHAKA AAPFNGTMMQ YFEWYLPDDG

                                                                                      79
            61                                                                        120
Am-Lich     QHWKRLQNDS AYLAEHGITA VWIPPAYKGT SQADVGYGAY DLYDLGEFHQ KGTVRTKYGT
Am-Amylo    QHWKRLQNDA EHLSDIGITA VWIPPAYKGL SQSDNGYGPY DLYDLGEFQQ KGTVRTKYGT
Am-Stearo   TLWTKVANEA NNLSSLGITA LSLPPAYKGT SRSDVGYGVY DLYDLGEFNQ KGTVRTKYGT

                                                                                      139
            121                                                                       180
Am-Lich     KGELQSAIKS LHSRDINVYG DVVINHKGGA DATEDVTAVE VDPADRNRVI SGEHLIKAWT
Am-Amylo    KSELQDAIGS LHSRNVQVYG DVVLNHKAGA DATEDVTAVE VNPANRNQET SEEYQIKAWT
Am-Stearo   KAQYLQAIQA AHAAGMQVYA DVVFDHKGGA DGTEWVDAVE VNPSDRNQEI SGTYQIQAWT

                                                                                      197
            181                                                                       240
Am-Lich     HFHFPGRGST YSDFKWHWYH FDGTDWDESR KLNRIYKF.... QGKAWDWEVS NENGNYDYLM
Am-Amylo    DFRFPGRGNT YSDFKWHWYH FDGADWDESR KISRIFKFRG EGKAWDWEVS SENGNYDYLM
Am-Stearo   KFDFPGRGNT YSSFKWRWYH FDGVDWDESR KLSRIYKFRG IGKAWDWEVD TENGNYDYLM

                                                                                      257
            241                                                                       300
Am-Lich     YADIDYDHPD VAAEIKRWGT WYANELQLDG FRLDAVKHIK FSFLRDWVNH VREKTGKEMF
Am-Amylo    YADVDYDHPD VVAETKKWGI WYANELSLDG FRIDAAKHIK FSFLRDWVQA VRQATGKEMF
Am-Stearo   YADLDMDHPE VVTELKNWGK WYVNTTNIDG FRLDGLKHIK FSFFPDWLSY VRSQTGKPLF

                                                                                      317
            301                                                                       360
Am-Lich     TVAEYWQNDL GALENYLNKT NFNHSVFDVP LHYQFHAAST QGGGYDMRKL LNGTVVSKHP
Am-Amylo    TVAEYWQNNA GKLENYLNKT SFNQSVFDVP LHFNLQAASS QGGGYDMRRL LDGTVVSRHP
Am-Stearo   TVGEYWSYDI NKLHNYITKT NGTMSLFDAP LHNKFYTASK SGGAFDMRTL MTNTLMKDQP
```

FIG._5A

```
                                                                                          377
           361                                                                            420
Am-Lich    LKSVTFVDNH DTQPGQSLES TVQTWFKPLA YAFILTRESG YPQVFYGDMY GTKGDSQREI
Am-Amylo   EKAVTFVENH DTQPGQSLES TVQTWFKPLA YAFILTRESG YPQVFYGDMY GTKGTSPKEI
Am-Stearo  TLAVTFVDNH DTNPAKR..CS HGRPWFKPLA YAFILTRQEG YPCVFYGDYY GI.........PQYNI

                                                                                          437
           421                                                                            480
Am-Lich    PALKHKIEPI LKARKQYAYG AQHDYFDHHD IVGWTREGDS SVANSGLAAL ITDGPGGAKR
Am-Amylo   PSLKDNIEPI LKARKEYAYG PQHDYIDHPD VIGWTREGDS SAAKSGLAAL ITDGPGGSKR
Am-Stearo  PSLKSKIDPL LIARRDYAYG TQHDYLDHSD IIGWTREGVT EKPGSGLAAL ITDGAGRSKW

                                                       483
           481                                                                            540
Am-Lich    MYVGRQNAGE TWHDITGNRS EPVVINSEGW GEFHVNGGSV SIYVQR......... ....................
Am-Amylo   MYAGLKNAGE TWYDITGNRS DTVKIGSDGW GEFHVNDGSV SIYVQK......... ....................
Am-Stearo  MYVGKQHAGK VFYDLTGNRS DTVTINSDGW GEFKVNGGSV SVWVPRKTTV STIARPITTR

           541                 559
Am-Lich    ........................ .................
Am-Amylo   ........................ .................
Am-Stearo  PWTGEFVRWH EPRLVAWP*
```

FIG._5B

| FIG._5A |
| --- |
| FIG._5B |

FIG._5

MODIFIED α-AMYLASES HAVING ALTERED CALCIUM BINDING PROPERTIES

FIELD OF THE INVENTION

The present invention is directed to α-amylases having altered calcium binding properties. Particularly, the present invention is directed to novel α-amylase enzymes having modifications thereto, for example point mutations, which are intended to alter the binding of calcium at a previously unknown calcium binding site in the molecule. By altering the calcium binding properties at this additional site, it is possible to improve the stability of the modified α-amylase.

BACKGROUND OF THE INVENTION

α-Amylases (α-1,4-glucan-4-glucanohydrolase, EC 3.2.1.1) hydrolyze internal α-1,4-glucosidic linkages in starch, largely at random, to produce smaller molecular weight malto-dextrins. α-Amylases are of considerable commercial value, being used in the initial stages (liquefaction) of starch processing; in alcohol production; as cleaning agents in detergent matrices; and in the textile industry for starch desizing. α-Amylases are produced by a wide variety of microorganisms including Bacillus and Aspergillus, with most commercial amylases being produced from bacterial sources such as *Bacillus licheniformis, Bacillus amyloliquefaciens, Bacillus subtilis* or *Bacillus stearothermophilus.* In recent years, the preferred enzymes in commercial use have been those from *Bacillus licheniformis* because of their heat stability and performance, at least at neutral and mildly alkaline pH's.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene or a-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO95/10603, α-amylase variants are disclosed which have improved laundry or dishwashing performance and comprise a mutation other than a single mutation at position M197 in *Bacillus licheniformis* α-amylase.

In PCT Publication No. WO94/02597, a mutant α-amylase having improved oxidative stability is described wherein one or more methionines are replaced by any amino acid except cysteine or methionine.

In PCT Publication No. WO94/18314, a mutant α-amylase having improved oxidative stability is described wherein one or more of the methionine, tryptophan, cysteine, histidine or tyrosine residues is replaced with a non-oxidizable amino acid.

In PCT Publication No. WO 91/00353, the performance characteristics and problems associated with liquefaction with wild-type *Bacillus licheniformis* α-amylase are approached by genetically engineering the α-amylase to include the specific substitutions Ala-111-Thr, His-133-Tyr and/or Thr-149-Ile.

Studies using recombinant DNA techniques to explore which residues are important for the catalytic activity of amylases and/or to explore the effect of modifying certain amino acids within the active site of various amylases and glycosylases have been conducted by various researchers (Vihinen et al., J. Biochem., vol. 107, pp. 267–272 (1990); Holm et al., Protein Engineering, vol. 3, pp. 181–191 (1990); Takase et al., Biochemica et Biophysica Acta, vol. 1120, pp. 281–288 (1992); Matsui et al., Febs Letters, vol. 310, pp. 216–218 (1992); Matsui et al., Biochemistry, vol. 33, pp. 451–458 (1992); Sogaard et al., J. Biol. Chem., vol. 268, pp. 22480–22484 (1993); Sogaard et al., Carbohydrate Polymers, vol. 21, pp. 137–146 (1993); Svensson, Plant Mol. Biol., vol. 25, pp. 141–157 (1994); Svensson et al., J. Biotech. vol. 29, pp. 1–37 (1993)). Researchers have also studied which residues are important for thermal stability (Suzuki et al., J. Biol. Chem., vol. 264, pp. 18933–18938 (1989); Watanabe et al., Eur. J. Biochem., vol. 226, pp. 277–283 (1994)); and one group has used such methods to introduce mutations at various histidine residues in a *Bacillus licheniformis* amylase, the rationale being that *Bacillus licheniformis* amylase, which is known to be relatively thermostable when compared to other similar Bacillus amylases, has an excess of histidines and, therefore, it was suggested that replacing a histidine could affect the thermostability of the enzyme. This work resulted in the identification of stabilizing mutations at the histidine residue at the +133 position and the alanine residue at position +209 (Declerck et al., J. Biol. Chem., vol. 265, pp. 15481–15488 (1990); FR 2 665 178-A1; Joyet et al., Bio/Technology, vol. 10, pp. 1579–1583 (1992)).

α-Amylases from different organisms have been shown to exhibit similar three-dimensional structure despite considerable differences in primary structure. FIG. 1 illustrates the structure of α-amylase of *Bacillus licheniformis.* While some inter-species variation will exist between the various α-amylases, it is believed that the major structural elements of *Bacillus licheniformis* α-amylase are representative of α-amylase structures in general (see Brayer et al., Protein Sci., vol. 4, pp. 1730–1742 (1995); Larson et al., J. Mol. Biol., vol. 235, pp. 1560–1584 (1994); Qian et al., J. Mol. Biol., vol. 231, pp. 785–799 (1993)). For example, site-specific mutagenesis has identified three invariant carboxylates and two invariant histidines (D231, E261, D328 and H104 and H327 in *Bacillus licheniformis* α-amylase), important for catalysis (Svensson, Plant Mol. Biol., vol. 25, p. 141 (1994)), and a general mechanism has been proposed (Mazur et al., Biochem. Biophys. Res. Comm., vol. 204, p. 297 (1994)). Residues found which are believed to be implicated in calcium and chloride binding have been characterized and found to be highly conserved among the different enzymes (see, e.g., Kadziola et al., J. Mol. Biol., vol. 239, p. 104 (1994); Qian et al., supra; Larson et al., supra; Brayer et al., supra; Machius et al., J. Mol. Biol., vol. 246, pp. 545–559 (1995); and Boel et al., Biochem., vol. 29, p. 6244 (1990)).

Moreover, homologies have been found between almost all endo-amylases sequenced to date, ranging from plants, mammals and bacteria (Nakajima et al., Appl. Microbiol. Biotechnol., vol. 23, pp. 355–360 (1986); Rogers, Biochem. Biophys. Res. Commun., vol. 128, pp. 470–476 (1985); Janecek, Eur. J. Biochem., vol. 224, pp. 519–524 (1994)). There are four areas of particularly high homology in certain Bacillus amylases, as shown in FIG. 5, wherein the underlined sections designate the areas of high homology. Sequence alignments have also been used to map the relationship between Bacillus endo-amylases (Feng et al., J.

Molec. Evol., vol. 35, pp. 351–360 (1987)). The relative sequence homology between *Bacillus stearothermophilus* and *Bacillus licheniformis* amylase is about 66% and that between *Bacillus licheniformis* and *Bacillus amyloliquefaciens* amylases is about 81%, as determined by Holm et al., Protein Engineering, vol. 3, no. 3, pp. 181–191 (1990). While sequence homology is important, it is generally recognized that structural homology is also important in comparing amylases or other enzymes.

Three dimensional structure similarities between various α-amylases (and related amylolytic enzymes like cyclodextrin glcosyltransferases and α-glucosidases) from different organisms, despite differences in their primary structure, are found in the common presence of an α/β-barrel forming a central part (domain A), a Greek key motif as a separate domain C and at least one additional domain, domain B (Machius et al., supra). Substrate binding is believed to be localized to a cleft between the α/β-barrel and domain B, comprising several β strands of variable length, depending on the species (Machius, supra). Also common is a requirement for calcium which is believed to maintain structural integrity. Machius discloses a calcium binding site implicating residues corresponding to N104, D200 and H235 derived from the crystal structure of a calcium depleted α-amylase from *Bacillus licheniformis*. In addition to the structure for *Bacillus licheniformis*, the structures for *Aspergillus niger* (Brady et al., Acta Crystallog. B, vol. 47, p. 527 (1991)), pig pancreas (Qian et al., J. Mol. Biol., vol. 231, p. 758 (1993); Larson et al., J. Mol. Biol., vol. 235, p. 1560 (1994)), and human pancreas (Brayer et al., Prot. Sci., vol. 4, p. 1730 (1995)) have been determined.

Despite the advances made in the prior art, a need exists for an α-amylase which has altered performance, including activity and stability, to facilitate their use in starch liquefaction, detergents for laundry and dishwashing, baking, textile desizing and other standard uses for amylase. Because commercially available amylases are not acceptable under many conditions due to stability and/or activity problems, there is a need for an amylase having altered, and preferably increased, performance profiles under such conditions. For example, high alkalinity and oxidant (bleach) levels associated with detergents or the extreme conditions present during starch liquefaction can result in both destabilization and lack of activity from α-amylase. Thus, altered performance characteristics such as thermostability, pH stability, oxidative stability or calcium stability which can be achieved while also altering, maintaining, or increasing enzymatic activity as compared to the wild-type or precursor enzyme, would be desirable. Similarly, many α-amylases are known to require the addition of calcium ion for stability. This is undesirable in some applications due to increased processing costs.

SUMMARY OF THE INVENTION

It is an object of the present invention to provide an α-amylase having altered performance profiles, e.g., altered pH stability, alkaline stability, oxidative stability, thermal stability or enzymatic activity.

It is a further object of the invention to provide an α-amylase having altered calcium binding properties, for example, having reduced need for added calcium to maintain activity levels.

It is a further object of the present invention to provide an α-amylase having improved performance due to increased low pH stability or activity, especially during liquefaction of starch.

It is still a further object of the present invention to provide an α-amylase having improved performance in high temperature or pH environments or in the presence of oxidants or bleach.

It is still a further object of the present invention to provide an α-amylase having improved performance in textile desizing or baking due to altered stability or activity.

According to the present invention, an α-amylase is provided comprising an A domain, a C domain and a calcium binding site, wherein the calcium binding site is associated with the A domain and the C domain and comprises ligand residues in the A domain and/or the C domain, wherein the α-amylase is modified to alter the characteristics of the calcium binding site and thereby alter the performance of the α-amylase.

In a preferred embodiment, the modification comprises a genetic modification resulting in a substitution, deletion or addition at a residue equivalent to one or more of amino acid residues 290–309, 339–347, 402–411, 426–436 or 472–477 in *Bacillus licheniformis* α-amylase. In an especially preferred embodiment, the genetic modification comprises substitution, deletion or addition at a residue equivalent to one or more of G301, M304, H405, H406 and/or K436 in *Bacillus licheniformis* α-amylase.

In a composition embodiment, the present invention comprises a DNA which encodes the α-amylase of the invention. In a further composition embodiment, the present invention comprises an expression vector incorporating a DNA which encodes the α-amylase according to the invention, as well as a host cell into which such DNA and/or expression vector has been transformed. A method embodiment comprises expressing a DNA encoding the α-amylase of the invention or an expression vector incorporating such DNA in a host cell.

In a further composition embodiment, the present invention comprises a laundry or dishwashing detergent composition which incorporates the α-amylase according to the invention. In another composition embodiment, the present invention comprises a textile desizing composition which incorporates the α-amylase according to the invention. In yet another composition embodiment, the present invention comprises a starch liquefaction composition which incorporates the α-amylase according to the invention. In yet another composition embodiment, the present invention comprises a baking aid comprising the α-amylase according to the invention.

In a process embodiment of the present invention, a method of laundering clothing or washing dishes with a dishwashing detergent composition which incorporates the α-amylase according to the invention is provided. In another process embodiment of the present invention, a method of desizing textiles with a composition which incorporates the α-amylase according to the invention is provided. In yet another process embodiment of the present invention, a method of liquefying starch with a starch liquefaction composition which incorporates the α-amylase according to the invention is provided. In yet another process embodiment of the present invention, a method of baking is provided comprising adding a composition which incorporates the α-amylase according to the invention.

The modified α-amylases according to the present invention will provide several important advantages when compared to prior art α-amylases. For example, one advantage is found in variants having increased activity at low pH and high temperatures typical of common starch liquefaction methods. Another advantage is found in variants having increased high pH and oxidative stability which facilitates their use in detergents. Yet another advantage is provided by variants having improved stability in the absence or low concentration of calcium ion. The objects and attendant advantages of the present invention will be made more clear in the following detailed description and examples.

BRIEF DESCRIPTION OF THE DRAWINGS

FIG. 1 illustrates the structure of *Bacillus licheniformis* α-amylase showing the main-chain folding and the location of the calcium binding site associated with the A domain and the B domain (CalA) and a second calcium binding site associated with the A domain and the C domain (CalB).

FIG. 2 illustrates the stereo view of the final 2fo-fc difference map and the Sm anomalous difference Fourier at the calcium binding site associated with the A domain and the C domain of α-amylase derived from *Bacillus licheniformis.*

FIGS. 3A–C illustrate the DNA sequence of the gene for α-amylase from *Bacillus licheniformis* (NCIB 8061) and deduced amino acid sequence of the translation product as described by Gray et al., J. Bacteriology, vol. 166, pp. 635–643 (1986).

FIG. 4 illustrates the amino acid sequence of the mature α-amylase enzyme from *Bacillus licheniformis.*

FIGS. 5A–B illustrate an alignment of the primary structures of three Bacillus α-amylases. The *Bacillus licheniformis* α-amylase (Am-Lich) is described by Gray et al., J. Bacteriology, vol. 166, pp. 635–643 (1986); the *Bacillus amyloliquefaciens* α-amylase (Am-Amylo) is described by Takkinen et al., J. Biol. Chem., vol. 258, pp. 1007–1013 (1983); and the *Bacillus stearothermophilus* α-amylase (Am-Stearo) is described by Ihara et al., J. Biochem., vol. 98, pp. 95–103 (1985).

DETAILED DESCRIPTION OF THE INVENTION

"α-Amylase" means an enzymatic activity which cleaves or hydrolyzes the α(1–4) glycosidic bond, e.g., that in starch, amylopectin or amylose polymers. α-Amylase as used herein includes naturally occurring α-amylases as well as recombinant α-amylases. The α-amylases according to the present invention may be derived from a precursor amylase. The precursor α-amylase is produced by any source capable of producing α-amylase. Suitable sources of α-amylases are prokaryotic or eukaryotic organisms, including fungi, bacteria, plants or animals. Preferably, the precursor α-amylase is produced by a Bacillus species such as *Bacillus amyloliquefaciens* or *Bacillus stearothermophilus*; more preferably, the precursor α-amylase is derived from *Bacillus licheniformis.*

A "modified" α-amylase is an α-amylase which has been subjected to genetic or chemical modification so as to change its biochemical, structural or physico-chemical properties. A "genetic modification" in α-amylase means that the DNA sequence encoding a naturally occurring or precursor α-amylase has been modified to produce a mutant DNA sequence which encodes the substitution, insertion or deletion of one or more amino acids in the α-amylase sequence compared to the naturally occurring α-amylase or a precursor α-amylase.

"Expression vector" means a DNA construct comprising a DNA sequence which is capable of effecting the expression of said DNA in a suitable host, generally being operably linked to a suitable control sequence. Such control sequences may include a promoter to effect transcription, an optional operator sequence to control such transcription, a sequence encoding suitable mRNA ribosome-binding sites, and sequences which control termination of transcription and translation. A preferred promoter is the *Bacillus subtilis* aprE promoter. The vector may be a plasmid, a phage particle, or DNA intended to effect genomic insertion, i.e., integration. Once transformed into a suitable host, the vector may replicate and function independently of the host genome, or may, in some instances, integrate into the genome itself. Plasmid and vector are sometimes used interchangeably as the plasmid is the most commonly used form of vector at present. However, the invention is intended to include such other forms of expression vectors which serve equivalent functions and which are, or become, known in the art, particularly including phage display.

"Host strain" or "host cell" means a suitable host for, e.g., an expression vector comprising DNA encoding the α-amylase according to the present invention. Host cells useful in the present invention are generally procaryotic or eucaryotic hosts, including any transformable microorganism in which the expression of α-amylase according to the present invention can be achieved. Specifically, host strains of the same species or genus from which the α-amylase is derived are suitable, such as a Bacillus strain. Preferably, an α-amylase negative Bacillus strain (genes deleted) and/or an α-amylase and protease deleted Bacillus strain (e.g., ΔamyE, Δapr, Δnpr) is used. Host cells are transformed or transfected with vectors constructed using recombinant DNA techniques. Such transformed host cells are capable of either replicating vectors encoding the α-amylase and its variants (mutants) or expressing the desired α-amylase.

"Liquefaction" or "liquefy" means a process by which starch is converted to shorter chain and less viscous dextrins. Generally, this process involves gelatinization of starch simultaneously with or followed by the addition of α-amylase.

"Calcium binding site" means a region within α-amylase which is suitable for and acts to bind a calcium ion in the presence of free calcium. Calcium is generally believed to be required to maintain the structural integrity of α-amylase under many conditions and the amino acid residues involved in calcium binding have been shown to be highly conserved among the different enzymes (Machius et al., J. Mol. Biol., vol. 246, pp. 545–559 (1995)). According to the present invention, the characteristics of the calcium binding site are altered compared to a wild-type or precursor α-amylase so as to alter the performance of the α-amylase. Alteration of the calcium binding site may include reducing or increasing the affinity of the site to bind calcium ion. By altering the performance is intended to mean the stability (e.g., oxidative or thermal) or the activity (e.g., the rate or efficiency with which the α-amylase hydrolyzes starch substrate) of the enzyme in its various applications.

"Ligand residues" or "calcium ligand" means an amino acid residue or residues within an α-amylase enzyme which forms a ligand with calcium ion bound within a calcium binding site. With respect to the calcium binding site within α-amylase discovered by Applicants, five amino acid ligands have been identified which are believed to act as calcium ligands. The calcium ligand residues comprise amino acid residues equivalent to G300, Y302, H406, D407 and D430 in *Bacillus licheniformis* α-amylase. Specifically with respect to these identified calcium ligands, the carbonyl oxygens of G300, Y302 and H406 and the side-chains of D407 and D430 are believed to be implicated in binding calcium.

According to the present invention, an α-amylase comprising an A domain, a C domain, and a calcium binding site is provided, wherein the calcium binding site is associated with the A domain and the C domain and comprises ligand residues in the A domain and/or the C domain, wherein the α-amylase is modified to alter the characteristics of the calcium binding site and thereby alter the performance of the α-amylase.

Also provided is a nucleic acid molecule (DNA) which encodes an amino acid sequence comprising at least a part of the α-amylase provided by the present invention, expression systems incorporating such DNA including vectors and phages, host cells transformed with such DNA, and anti-sense strands of DNA corresponding to the DNA molecule which encodes the amino acid sequence. Similarly, the present invention includes a method for producing an α-amylase by expressing the DNA incorporated on an expression system which has been transformed into a host cell.

The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose. In addition, any of a wide variety of expression control sequences are generally used in these vectors. For example, Applicants have discovered that a preferred expression control sequence for Bacillus transformants is the aprE signal peptide derived from *Bacillus subtilis*. Additionally, phage display systems are useful for the invention herein.

A wide variety of host cells are also useful in expressing the DNA sequences of this invention and are contemplated herein. These hosts may include well known eukaryotic and prokaryotic hosts, such as strains of *E. coli*, Pseudomonas, Bacillus, Streptomyces, various fungi, e.g., Trichoderma or Aspergillus, yeast and animal cells. Preferably, the host expresses the α-amylase of the present invention extracellularly to facilitate purification and downstream processing. Expression and purification of the mutant α-amylase of the invention may be effected through art-recognized means for carrying out such processes.

The α-amylases according to the present invention comprise an amino acid sequence which is derived from the amino acid sequence of a precursor α-amylase. The precursor α-amylases include naturally occurring α-amylases and recombinant α-amylases. The amino acid sequence of the α-amylase mutant is derived from the precursor α-amylase amino acid sequence by the substitution, deletion or insertion of one or more amino acids of the precursor amino acid sequence. Such modification is generally of the precursor DNA sequence which encodes the amino acid sequence of the precursor α-amylase rather than manipulation of the precursor α-amylase enzyme per se. Methods for modifying α-amylase genes (i.e., through site-directed oligonucleotide mutagenesis) and transforming, expressing and secreting enzyme products produced pursuant to the mutagenized gene have been described in the prior art, including PCT Publication No. WO95/10603 (Novo Nordisk), PCT Publication No. WO94/02597 (Novo Nordisk), PCT Publication No. WO94/18314 (Genencor International, Inc.) and PCT Publication No. WO91/00353 (Gist Brocades), such disclosures being incorporated by reference. Additional suitable methods for manipulation of the precursor DNA sequence include methods disclosed herein and in commonly owned U.S. Pat. Nos. 4,760,025 and 5,185,258, incorporated herein by reference.

The major structural elements, including the newly discovered CalB site which is disclosed herein, and changes thereto to alter the performance of an α-amylase are described below in general terms as applicable to most α-amylases. As shown in FIG. 1, three major domains are defined, the A domain, the B domain and the C domain, as well as two calcium binding sites, CalA and CalB. The A domain comprises the central portion of the molecule and has been identified as an α/β or TIM barrel. The α/β barrel is made of a series of parallel β-strands which are interconnected by α-helices. On the carboxyl end of the enzyme on one side of the A domain is a region comprising an anti-parallel β-barrel known as a "Greek key" motif (see, e.g., Richardson et al., Advan. Protein Chem., vol. 34, 167–339 (1981); Braden et al., Introduction to Protein Structure, Garland Publishing Inc., New York (1991)). This domain has been identified as the C domain. On the opposite side of the A domain from the C domain (the N-terminal) is an additional domain which comprises several β strands of variable length depending on the species, known as the B domain. The B domain has been recognized as being highly variable between α-amylases of different species and often comprises extended loops. It is believed that substrate binding is localized to a cleft between the A domain and the B domain and that the active site is further associated with this region of the molecule. The CalA binding site is located within a cleft separating the A domain and the B domain and is believed to provide stability to this region. The CalB binding site disclosed herein is located in the region where the A domain and the C domain interface.

The discovery of the CalB binding site in a Bacillus α-amylase by Applicants has enabled Applicants to develop mutant α-amylases having altered performance, and particularly altered stability. For example, general principles for stabilization of protein structure may be applied to the region around the CalB site. Additionally, strategies specifically designed to improve calcium binding at the CalB site may be implemented to increase the stability of the enzyme. Preferably, such modifications are within 15 angstroms of the center of mass of the calcium bound to the CalB binding site, more preferably within 10 angstroms of the center of mass of the calcium bound to the CalB binding site.

Residues in α-amylase are identified herein for deletion or substitution. Thus, specific residues discussed herein refer to an amino acid position number which references the number assigned to the mature *Bacillus licheniformis* α-amylase sequence illustrated in FIG. 4. The invention, however, is not limited to the mutation of the particular mature α-amylase of *Bacillus licheniformis* but extends to non-*Bacillus licheniformis* precursor α-amylases containing amino acid residues at positions which are equivalent to the particular identified residue in *Bacillus licheniformis* α-amylase. A residue of a precursor α-amylase is equivalent to a residue of *Bacillus licheniformis* α-amylase if it is either homologous (i.e., corresponds in position for either the primary or tertiary structure) or analogous to a specific residue or portion of that residue in *Bacillus licheniformis* α-amylase (i.e., having the same or similar functional capacity to combine, react, or interact chemically or structurally).

In order to establish homology to primary structure, the amino acid sequence of a precursor α-amylase is directly compared to the *Bacillus licheniformis* α-amylase primary sequence and particularly to a set of residues known to be invariant to all α-amylases for which sequences are known (see, e.g., FIG. 7). It is possible also to determine equivalent residues by tertiary structure analysis of the crystal structures reported for porcine pancreatic α-amylase (Buisson et al., EMBO Journal, vol. 6, pp. 3909–3916 (1987); Qian et al., Biochemistry, vol. 33, pp. 6284–6294 (1994); Larson et al., J. Mol. Biol., vol. 235, pp. 1560–1584 (1994)); Taka-amylase A from *Aspergillus oryzae* (Matsuura et al., J. Biochem. (Tokyo), vol. 95, pp. 697–702 (1984)); and an acid α-amylase from *A. niger* (Boel et al., Biochemistry, vol. 29, pp. 6244–6249 (1990)), with the former two structures being similar, and for barley α-amylase (Vallee et al., J. Mol. Biol., vol. 236, pp. 368–371 (1994); Kadziola, J. Mol. Biol., vol. 239, pp. 104–121 (1994)). Although there have been some preliminary studies published (Suzuki et al., J. Biochem., vol. 108, pp. 379–381 (1990); Lee et al., Arch. Biochem. Biophys, vol. 291, pp. 255–257 (1991); Chang et al., J. Mol. Biol., vol. 229, pp. 235–238 (1993); Mizuno et al., J. Mol. Biol., vol. 234, pp. 1282–1283 (1993)), there is only a published structure for *Bacillus licheniformis* α-amylase (Machius et al., J. Mol. Biol. vol. 246, pp. 545–549 (1995)). However, several researchers have predicted common super-secondary structures between glucanases (MacGregor et al., Biochem. J., vol. 259, pp. 145–152 (1989)) and within α-amylases and other starch-metabolizing enzymes (Jaspersen, J. Prot. Chem. vol. 12, pp. 791–805 (1993); MacGregor, Starke, vol. 45, pp. 232–237 (1993)); and sequence similarities between enzymes with similar super-secondary structures to α-amylases (Janecek, FEBS Letters, vol. 316, pp. 23–26 (1993); Janecek et al., J. Prot. Chem., vol. 12, pp. 509–514 (1993)). A structure for the *Bacillus stearothermophilus* enzyme has been modeled on that of Taka-amylase A (Holm et al., Protein Engineering, vol. 3, pp. 181–191 (1990)). The four highly conserved regions shown in FIG. 7 contain many residues thought to be part of the active-site (Matsuura et al., J. Biochem. (Tokyo), vol. 95, pp. 697–702 (1984); Buisson et al., EMBO Journal, vol. 6, pp. 3909–3916 (1987); Vihinen et al., J. Biochem., vol. 107, pp. 267–272 (1990)) including His +105; Arg +229; Asp +231; His +235; Glu +261 and Asp +328 under the *Bacillus licheniformis* numbering system.

The segments of the α-amylase polypeptide chain which comprise the CalB binding site include residues 290–309, 339–347, 402–411, 426–436 and 472–477. These polypeptide segments comprise the CalB binding site. Accordingly, regiospecific random mutations in these regions would be expected to yield variants that modulate the stability of α-amylase via modulation of the affinity of calcium at this site.

Additional more specific strategies are provided below:

(1) Increasing the entropy of main-chain unfolding may introduce stability to the enzyme. For example, the introduction of proline residues into position 2 of reverse turns at the N-termini of α-helices and in loop structures may significantly stabilize the protein by increasing the entropy of the unfolding (see, e.g., Watanabe et al., Eur. J. Biochem., vol. 226, pp. 277–283 (1994)). Similarly, glycine residues have no β-carbon, and thus have considerably greater backbone conformational freedom than many other residues. This may lead to high flexibility with resultant weak stability. Replacement of glycines at one or more residues equivalent to G299, G410, G433, G474, G475 in *Bacillus licheniformis*, preferably with an alanine, may reduce the flexibility and improve stability. Additionally, by shortening external loops it may be possible to improve stability. It has been observed that hyperthermophile produced proteins have shorter external loops than their mesophilic homologues (see, e.g., Russel et al., Current Opinions in Biotechnology, vol. 6, pp. 370–374 (1995). The introduction of disulfide bonds may also be effective to stabilize distinct tertiary structures in relation to each other. Modification at G301 would alter the stability of the segment at 290–309 by restricting or improving the conformational variability of glycine. Specifically contemplated are substitutions of aspartic acid or proline at this residue. Modification at G474 by replacement with another residue may increase stability by introducing a Cβ, thus lowering its conformational freedom.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, Ann. Rev. Biochem., vol. 62, pp. 139–160 (1993); Burley et al., Science, vol. 229, pp. 23–29 (1985); Zuber, Biophys. Chem., vol. 29, pp. 171–179 (1988); Kellis et al., Nature, vol. 333, pp. 784–786 (1988)). It is known that multimeric proteins from thermophiles often have more hydrophobic sub-unit interfaces with greater surface complementarity than their mesophilic counterparts (Russel et al., supra). This principle is believed by Applicants to be applicable to domain interfaces of monomeric proteins. Specific substitutions that may improve stability by increasing hydrophobicity include lysine to arginine, serine to alanine and threonine to alanine (Russel et al., supra). Modification at G301 by substitution to alanine or proline may increase side-chain size with resultant reduction in cavities, better packing and increased hydrophobicity. Additionally, a cavity at the interface between domain A and domain C in the CalB binding region is bordered by Y302, M304, L307, F343, L427 and I428. Substitutions to reduce the size of the cavity, increase hydrophobicity and improve the complementarity of the A domain-C domain interface may improve stability of the enzyme. Specifically, modification of the specific residue at these positions with a different residue selected from any of phenylalanine, tryptophan, tyrosine, leucine and isoleucine may improve performance. Additional substitutions which may be useful are at V409 and F403, preferably the substitutions at V409 comprise isoleucine or leucine, and at F403 comprise tyrosine or tryptophan.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson et al., Science, vol. 255, pp. 178–183 (1992)). Similarly, neutralizing partial negative charges on helix C-terminus with positive charge may improve stability. Removing positive charge from interacting with peptide N-terminus in β-turns should be effective in conferring tertiary structure stability. Substitution of H405 with a non-positively charged residue could remove an unfavorable positive charge from interacting with the amide nitrogen of D407 in the 405–408 turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner et al., Biochemistry, vol. 35, pp. 2597–2609). Substitution of H405 with aspartic acid, asparagine, glutamic acid or glutamine may introduce a hydrogen bond with the backbone amide of D407, thus stabilizing the 405–408 turn. Substitution at K436 with arginine may improve the salt bridge with D404 and introduce an H-bond into the backbone carbonyl of I408.

(5) Avoiding thermolabile residues in general may increase thermal stability. For example, asparagine and glutamine are susceptible to deamidation and cysteine is susceptible to oxidation at high temperature. Reducing the number of these residues in sensitive positions may result in improved thermostability (Russel et al., supra). Substitution or deletion at Q291, Q298, N309, Q340 or N473 by any residue other than glutamine or cysteine may increase stability by avoidance of a thermolabile residue.

(6) Introducing a sixth ligand from the protein to the calcium ion may improve the stability of the bound calcium and, thus, the enzyme. Substitution of H406 with aspartic acid, asparagine, glutamic acid or glutamine may increase the calcium affinity.

(7) Stabilization of the existing ligands to calcium in CalB may also improve stability of the bound calcium and, thus, the enzyme. For example, M304 may be substituted with phenylalanine or tyrosine to introduce aromatic side-chain/aspartic acid side-chain stabilization where the carboxylate oxygen may interact favorably with the partial positive charge associated with benzyl rings, increasing the stability of D407 and D430. Substitution of H405 with phenylalanine or tyrosine to introduce a hydrophobic group near D407, may increase the stability of D407 via formation of favorable van der Waals interactions with C-b and C-g atoms of the D407 side-chain. Substitution at G300 with phenylalanine may remove the side-chain H-bond to Q291.

(8) Increasing the electronegativity of any of the calcium ligands may improve calcium binding. For example, substitution of M304 with phenylalanine or tyrosine may increase the electronegativity of D407 and D430 by improved shielding from solvent, thereby improving calcium binding.

(9) Removing positive-charges in the vicinity of the calcium ion that may interfere with the calcium binding should similarly improve the calcium binding site stability. For example, substituting H405 or H406, which are in the immediate vicinity of the bound calcium, may have positive charge that could produce unfavorable charge-charge interactions with the positively charged calcium ion and may have competing charge-charge interactions with negatively charged calcium ligands. Thus, replacement with a suitable non-positively charged residue may increase calcium affinity and protein stability.

(10) Stabilization of the CalB binding site by introducing negatively charged residues in the vicinity thereof may also improve the binding of the calcium ion in the site (see, e.g., Pantoliano et al., Biochemistry, vol. 27, pp. 8311–8317 (1988); Bryan, Stability of Protein Pharmaceuticals Part B: In vitro Pathways for Degradation and Strategies for Protein Stabilization (Ahern & Manning, Eds.), pp. 147–181 (1992); Fagain, Biochim. Biophys. Acta, vol. 1252, pp. 1–14 (1995) ). For example, substitution of Q291, Q298, N309, Q304, H405, H406, N473 and/or G474 with negatively charged aspartic acid or glutamic acid will increase the net negative charge in the calcium area and may increase calcium affinity and, thus, enzyme stability.

The α-amylases according to the present invention may exhibit altered performance characteristics providing desirable and unexpected results which are useful in the various applications for which α-amylases are commonly used. For example, α-amylases according to the present invention which exhibit altered performance characteristics at low pH, including improved thermostability, improved pH stability and/or improved oxidative stability, are useful in low pH liquefaction of starch. Enhanced thermostability will be useful in extending the shelf life of products which incorporate them. Enhanced oxidative stability or improved performance is particularly desirable in cleaning products, and for extending the shelf life of α-amylase in the presence of bleach, perborate, percarbonate or peracids used in such cleaning products. To the contrary, reduced thermal stability or oxidative stability may be useful in industrial processes which require the rapid and efficient quenching of amylolytic activity. Additionally, a reduced requirement or stronger affinity for calcium would be advantageous in the presence of sequestering components generally found in detergents, i.e., builders.

The α-amylase of the present invention is especially useful in starch processing and particularly in starch liquefaction. Conditions present during commercially desirable liquefaction processes characteristically include low pH, high temperature and potential oxidation conditions requiring α-amylases exhibiting improved low pH performance, improved thermal stability and improved oxidative stability. Accordingly, α-amylases according to the present invention which are particularly useful in liquefaction exhibit improved performance at a pH of less than about 6, preferably less than about 5.5, and more preferably between about 5.0 and 5.5. Additionally, α-amylases according to the present invention which exhibit increased thermal stability at temperatures of between about 80°–120° C., and preferably between about 100°–110° C., and increased stability in the presence of oxidants will be particularly useful. Preferably, the α-amylase according to the present invention which is used in liquefaction further comprises a deletion or substitution at one or more of positions M15, V128, H133, W138, N188, A209 and/or M197.

In another embodiment of the present invention there are provided detergent compositions in either liquid, gel or granular form, which comprise the α-amylase according to the present invention. Such detergent compositions will particularly benefit from the addition of an α-amylase according to the present invention which has increased thermal stability to improve shelf-life or increased oxidative stability such that the α-amylase has improved resistance to bleach or peracid compounds commonly present in detergents. Thus, α-amylase according to the present invention may be advantageously formulated into known powdered, liquid or gel detergents having a pH of between about 6.5 and about 12.0. A preferred embodiment of the present invention further comprises a deletion or substitution at one or more of positions M15, V128, H133, W138, N188, A209 and/or M197. Detergent compositions comprising the α-amylase according to the present invention may further include other enzymes such as endoglycosidases, cellulases, proteases, lipases or other amylase enzymes, for example amylase derived from *Bacillus stearothermophilus*, as is generally known in the art.

Embodiments of the present invention which comprise a combination of the α-amylase according to the present invention with protease enzymes preferably include oxidatively stable proteases such as those described in U.S. Pat. No. Re 34,606, incorporated herein by reference, as well as commercially available enzymes such as DURAZYM (Novo Nordisk), MAXAPEM (Gist-brocades) and PURAFECT® OxP (Genencor International, Inc.). Methods for making such protease mutants (oxidatively stable proteases), and particularly such mutants having a substitution for the methionine at a position equivalent to M222 in *Bacillus amyloliquefaciens*, are described in U.S. Pat. No. Re 34,606.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

Experimental

EXAMPLE

Preparation of *Bacillus licheniformis* α-Amylase Crystals

Crystals were grown in 10 μL hanging drops, from 1.6–1.8M $Li_2SO_4$, 1 mM $CaCl_2$, 50 mM NaCl, buffered at pH 6.5 with 200 mM bistrispropane. The crystals grow as elongated prisms, to a maximum dimension of approximately 1.5 mm, in 7–14 days. The space group is $P2_12_12_1$, with a=118.3Å, b=119.0Å and c=84.9Å. The Matthews No. (see Matthews, J., Mol. Biol., vol. 33, pp. 409 (1968)) is 3.01, assuming 2 molecules in the asymmetric unit, which is within the normal range. Data were recorded using an RAXISII image plate system, mounted on an RU-200B rotating anode X-generator, producing graphite monochromated $CuK_\alpha$ radiation. Data were processed and reduced to amplitudes using software distributed with the system by Molecular Structures Corp. (The Woodlands, Tex.). The phase information was determined using multiple isomorphous replacement (MIR) supplemented with anomalous scattering data (MIRAS), and subsequent density modification. Heavy-atom derivatives were prepared by conventional soaking methods, except for the $SmCl_3$, derivative, which was prepared by co-crystallization. Heavy-atom positions were located using difference Pattersons and cross-phased difference Fouriers. Excellent anomalous scattering data was obtained for a $SmCl_3$ derivative, which was used to find the correct hand, and put all heavy-atoms on a common origin. Heavy-atom positions were refined and MIRAS phases calculated, using Xheavy (Zhang et al., Acta Crystallog. A, vol. 46, pp. 377 (1990)). Phases were improved by solvent flattening, with SQUASH (McRee, J., Mol. Graph., vol. 10, pp. 44 (1992)), resulting in a 3.0Å map in which most of the secondary structure elements of both molecules could be identified. Model building, real space refinement and symmetry averaging were performed using Xfit (Zhang, supra). The Cα positions of the β-strands and α-helices of the α/β barrel domain, and the C-terminal of all β domains of both molecules were identified. The TIM barrel of Aspergillus α-amylase (PDB entry 6TM.) (Swift et al., Acta Crystallog. B, vol. 47, pp. 535 (1991)) was approximately overlaid the Cα trace of both molecules of the asymmetric unit and were accurately positioned using real-space refinement of the entire unmodified domain. This allowed accurate determination of the local symmetry operator, which was used for non-crystallographic symmetry averaging of the map. This resulted in a significant improvement of the map, except for domain B. At this point, only one molecule was built to the symmetry averaged map, the second being generated using the local symmetry operator. The Cα positions were identified, and the main-chain built using overlapping pentamers, drawn from a database of well refined structures (Zhang, supra; Jones et al., EMBO, vol. 5, pp. 819 (1986)). At domain B, much of the map was uninterpretable and only residues 105–116 and 133–169 could be built. Dummy alanines were built for those residues for which no side-chain density was evident. This initial model was refined using a simulated annealing slowcool protocol (initial temp=3000K), followed by conventional least-squares refinement, using Xplor (Brunger et al., Acta Crystallog. A, vol. 45, p. 50 (1989)) for data between 15–3.0Å (F≦3σ), with non-crystallographic symmetry restraints applied. This model converged at an R-factor of 0.28. MIRAS and model phases were combined using sigmaA (Read, Acta Crystallog. A, vol. 42, pp. 140 (1986)), to produce a 2.2Å map. Missing residues were built, along with considerable manual adjustment of the rest of the structure, and then refined using simulated annealing (initial temp=1000K), using data between 8.0 and 2.2Å (F≦3σ). The model converged at an R-factor of 0.245. Subsequent restrained isotropic B-factor refinement gave an R-factor of 0.225. SigmaA weighted 2fo-fc and fo-fc maps were computed using calculated phases and used to identify errors, and to locate the calcium ions. Upon obtaining 1.9Å native data, fo-fc and 2fo-fc difference maps were used to locate remaining errors and identify ordered water molecules, followed by Powell minimization and stereochemically restrained B-factor refinement.

The R-factor of the present model is 0.19, (15–1.9Å, F≦3σF). The model contains 7914 non-hydrogen atoms, and includes 630 water oxygen atoms, and three calcium atoms. It shows good geometry, with r.m.s deviations of 0.012Å and 1.35° from ideal bond lengths and angles, respectively. The Ramachandron plot of φ and ψ angles shows that residue 150 is the only non-glycine residue to deviate significantly from allowed regions.

*B. licheniformis* α-amylase contains 483 residues. In the present model the first three residues of the N-terminus and the C-terminal residue are missing. Also missing are residues 181–195 of molecule 1, and 181–193 of molecule 2. The data derived from this example is provided in Table 1.

TABLE 1

| Data set | Resolution | Rmerge | R-deriv. | N sites | Phasing power | Anom. Scatt. |
|---|---|---|---|---|---|---|
| Native | 50-1.8 Å | 0.09 | — | — | — | — |
| $SmCl_3$ | 50-2.2 Å | | 0.073 | 4 | 1.45 | Y |
| $PtI_6$ | 50-3.0 Å | | 0.259 | 5 | 1.22 | N |
| $PtCl_4$ | 50-3.0 Å | | 0.249 | 5 | 1.29 | N |
| $Hg(Ac)_2$ | 50-3.0 Å | | 0.124 | 4 | 1.33 | N |
| $IrCl_6$ | 50-3.0 Å | | 0.226 | 4 | 1.01 | N |
| $HgI_3$ | 50-2.2 Å | | 0.133 | 12[1] | 1.48 | Y |
| $Me_3PbI$ | 50-2.2 Å | | 0.186 | 2 | 1.29 | Y |

We claim:

1. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to one or more of, Q298, G299, G301, Y302, L307, N309, Q340, F343, F403, H405, H406, D407, , G410, L427, I428, D430, G433, K436, N473, G474 and G475 in *Bacillus licheniformis*.

2. The α-amylase according to claim 1, wherein said α-amylase is produced by Bacillus.

3. The α-amylase according to claim 2, wherein said α-amylase is produced by *Bacillus licheniformis, Bacillus amyloliquefaciens* or *Bacillus stearothermophilus*.

4. A detergent comprising the α-amylase according to claim 1.

5. A starch liquefaction composition comprising the α-amylase according to claim 1.

6. The α-amylase according to claim 1, wherein said α-amylase further comprises a substitution or deletion at one or more residues equivalent to M15, V128, H133, W138, N188, A209 and/or M197 in *Bacillus licheniformis*.

7. The α-amylase according to claim 1 which is modified by substituting an amino acid residue at a position corresponding to one or more of G301, H405, H406 and/or K436 in *Bacillus licheniformis*.

8. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to Q298 in *Bacillus licheniformis*.

9. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby alter the performance of said $\alpha$-amylase by substituting an amino acid residue at a position corresponding to G299 in *Bacillus licheniformis*.

10. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to G301 in *Bacillus licheniformis*.

11. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby alter the performance of said $\alpha$-amylase by substituting an amino acid residue at a position corresponding to Y302 in *Bacillus licheniformis*.

12. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby alter the performance of said $\alpha$-amylase by substituting an amino acid residue at a position corresponding to L307 in *Bacillus licheniformis*.

13. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby after the performance of said $\alpha$-amylase by substituting an amino acid residue at a position corresponding to N309 in *Bacillus licheniformis*.

14. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby alter the performance of said $\alpha$-amylase by substituting an amino acid residue at a position corresponding to Q340 in *Bacillus licheniformis*.

15. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to F343 in *Bacillus licheniformis*.

16. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to F403 in *Bacillus licheniformis*.

17. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to H405 in *Bacillus licheniformis*.

18. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to H406 in *Bacillus licheniformis*.

19. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby after the performance of said $\alpha$-amylase by substituting an amino acid residue at a position corresponding to D407 in *Bacillus licheniformis*.

20. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to G410 in *Bacillus licheniformis*.

21. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to after the characteristics of said calcium binding site and thereby alter the performance of said $\alpha$-amylase by substituting an amino acid residue at a position corresponding to L427 in *Bacillus licheniformis*.

22. An $\alpha$-amylase comprising an A domain, a C domain and a calcium binding site, wherein said calcium binding site is associated with said A domain and said C domain comprises ligand residues in said A domain and/or said C domain, wherein said $\alpha$-amylase is modified to alter the characteristics of said calcium binding site and thereby alter the performance of said $\alpha$-amylase by substituting an amino acid residue at a position corresponding to I428 in *Bacillus licheniformis*.

23. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to D430 in *Bacillus licheniformis*.

24. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to G433 in *Bacillus licheniformis*.

25. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to K436 in *Bacillus licheniformis*.

26. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby after the performance of said α-amylase by substituting an amino acid residue at a position corresponding to N473 in *Bacillus licheniformis*.

27. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to G474 in *Bacillus licheniformis*.

28. An α-amylase comprising an A domain, a C domain and a calcium binding site, wherein said calcium binding site is associated with said A domain and said C domain comprises ligand residues in said A domain and/or said C domain, wherein said α-amylase is modified to alter the characteristics of said calcium binding site and thereby alter the performance of said α-amylase by substituting an amino acid residue at a position corresponding to G475 in *Bacillus licheniformis*.

* * * * *

Adverse Decision In Interference

Patent No. 5,763,385, Richard R. Bott, Andrew Shaw, MODIFIED ALPHA-AMYLASES HAVING ALTERED CALCIUM BINDING PROPERTIES, Interference No. 105,206, final judgment adverse to the patentees rendered, November 10, 2005, as to claims 1-28.

*(Official Gazette, March 7, 2006)*

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 1968 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus licheniformis ( x i ) SEQUENCE DESCRIPTION: SEQ ID NO: 1:

```
AGCTTGAAGA AGTGAAGAAG CAGAGAGGCT ATTGAATAAA TGAGTAGAAA GCGCCATATC    60
GGCGCTTTTC TTTTGGAAGA AAATATAGGG AAAATGGTAC TTGTTAAAAA TTCGGAATAT   120
TTATACAACA TCATATGTTT CACATTGAAA GGGGAGGAGA ATCATGAAAC AACAAAAACG   180
GCTTTACGCC CGATTGCTGA CGCTGTTATT TGCGCTCATC TTCTTGCTGC CTCATTCTGC   240
AGCAGCGGCG GCAAATCTTA ATGGGACGCT GATGCAGTAT TTTGAATGGT ACATGCCCAA   300
TGACGGCCAA CATTGGAAGC GTTTGCAAAA CGACTCGGCA TATTTGGCTG AACACGGTAT   360
TACTGCCGTC TGGATTCCCC CGGCATATAA GGGAACGAGC CAAGCGGATG TGGGCTACGG   420
TGCTTACGAC CTTTATGATT TAGGGGAGTT TCATCAAAAA GGGACGGTTC GGACAAAGTA   480
CGGCACAAAA GGAGAGCTGC AATCTGCGAT CAAAAGTCTT CATTCCCGCG ACATTAACGT   540
TTACGGGGAT GTGGTCATCA ACCACAAAGG CGGCGCTGAT GCGACCGAAG ATGTAACCGC   600
GGTTGAAGTC GATCCCGCTG ACCGCAACCG CGTAATTTCA GGAGAACACC TAATTAAAGC   660
CTGGACACAT TTTCATTTTC CGGGGCGCGG CAGCACATAC AGCGATTTTA AATGGCATTG   720
GTACCATTTT GACGGAACCG ATTGGGACGA GTCCCGAAAG CTGAACCGCA TCTATAAGTT   780
TCAAGGAAAG GCTTGGGATT GGGAAGTTTC CAATGAAAAC GGCAACTATG ATTATTTGAT   840
GTATGCCGAC ATCGATTATG ACCATCCTGA TGTCGCAGCA GAAATTAAGA GATGGGGCAC   900
TTGGTATGCC AATGAACTGC AATTGGACGG TTTCCGTCTT GATGCTGTCA AACACATTAA   960
ATTTTCTTTT TTGCGGGATT GGGTTAATCA TGTCAGGGAA AAAACGGGGA AGGAAATGTT  1020
TACGGTAGCT GAATATTGGC AGAATGACTT GGGCGCGCTG GAAAACTATT TGAACAAAAC  1080
AAATTTTAAT CATTCAGTGT TTGACGTGCC GCTTCATTAT CAGTTCCATG CTGCATCGAC  1140
ACAGGGAGGC GGCTATGATA TGAGGAAATT GCTGAACGGT ACGGTCGTTT CCAAGCATCC  1200
GTTGAAATCG GTTACATTTG TCGATAACCA TGATACACAG CCGGGGCAAT CGCTTGAGTC  1260
GACTGTCCAA ACATGGTTTA AGCCGCTTGC TTACGCTTTT ATTCTCACAA GGGAATCTGG  1320
ATACCCTCAG GTTTTCTACG GGGATATGTA CGGGACGAAA GGAGACTCCC AGCGCGAAAT  1380
TCCTGCCTTG AAACACAAAA TTGAACCGAT CTTAAAAGCG AGAAAACAGT ATGCGTACGG  1440
AGCACAGCAT GATTATTTCG ACCACCATGA CATTGTCGGC TGGACAAGGG AAGGCGACAG  1500
CTCGGTTGCA AATTCAGGTT TGGCGGCATT AATAACAGAC GGACCCGGTG GGGCAAAGCG  1560
AATGTATGTC GGCCGGCAAA ACGCCGGTGA GACATGGCAT GACATTACCG GAAACCGTTC  1620
GGAGCCGGTT GTCATCAATT CGGAAGGCTG GGGAGAGTTT CACGTAAACG GCGGGTCGGT  1680
TTCAATTTAT GTTCAAAGAT AGAAGAGCAG AGAGGACGGA TTTCCTGAAG GAAATCCGTT  1740
```

```
TTTTTATTTT GCCCGTCTTA TAAATTTCTT TGATTACATT TTATAATTAA TTTTAACAAA   1800
GTGTCATCAG CCCTCAGGAA GGACTTGCTG ACAGTTTGAA TCGCATAGGT AAGGCGGGGA   1860
TGAAATGGCA ACGTTATCTG ATGTAGCAAA GAAAGCAAAT GTGTCGAAAA TGACGGTATC   1920
GCGGGTGATC AATCATCCTG AGACTGTGAC GGATGAATTG AAAAAGCT                1968
```

( 2 ) INFORMATION FOR SEQ ID NO: 2:

( i ) SEQUENCE CHARACTERISTICS:
( A ) LENGTH: 483 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Bacillus licheniformis ( x i ) SEQUENCE DESCRIPTION: SEQ ID NO: 2:

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Arg Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
```

-continued 290 295 300

Arg Lys Leu Leu Asn Ser Thr Val Val Ser Lys His Pro Leu Lys Ala
305 310 315 320

Val Thr Phe Val Asp Asn His Asp Thr Gln Pro Gly Gln Ser Leu Glu
325 330 335

Ser Thr Val Gln Thr Trp Phe Lys Pro Leu Ala Tyr Ala Phe Ile Leu
340 345 350

Thr Arg Glu Ser Gly Tyr Pro Gln Val Phe Tyr Gly Asp Met Tyr Gly
355 360 365

Thr Lys Gly Asp Ser Gln Arg Glu Ile Pro Ala Leu Lys His Lys Ile
370 375 380

Glu Pro Ile Leu Lys Ala Arg Lys Gln Tyr Ala Tyr Gly Ala Gln His
385 390 395 400

Asp Tyr Phe Asp His His Asp Ile Val Gly Trp Thr Arg Glu Gly Asp
405 410 415

Ser Ser Val Ala Asn Ser Gly Leu Ala Ala Leu Ile Thr Asp Gly Pro
420 425 430

Gly Gly Ala Lys Arg Met Tyr Val Gly Arg Gln Asn Ala Gly Glu Thr
435 440 445

Trp His Asp Ile Thr Gly Asn Arg Ser Glu Pro Val Val Ile Asn Ser
450 455 460

Glu Gly Trp Gly Glu Phe His Val Asn Gly Gly Ser Val Ser Ile Tyr
465 470 475 480

Val Gln Arg ( 2 ) INFORMATION FOR SEQ ID NO: 3:

( i ) SEQUENCE CHARACTERISTICS:
( A ) LENGTH: 511 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 3:

Met Lys Gln Gln Lys Arg Leu Tyr Ala Arg Leu Leu Thr Leu Leu Phe
1 5 10 15

Ala Leu Ile Phe Leu Leu Pro His Ser Ala Ala Ala Ala Ala Asn Leu
20 25 30

Asn Gly Thr Leu Met Gln Tyr Phe Glu Trp Tyr Met Pro Asn Asp Gly
35 40 45

His Trp Lys Arg Leu Gln Asn Asp Ser Ala Tyr Leu Ala Glu His Gly
50 55 60

Ile Thr Ala Val Trp Ile Pro Pro Ala Tyr Lys Gly Thr Ser Gln Ala
65 70 75 80

Asp Val Gly Tyr Gly Ala Tyr Asp Leu Tyr Asp Leu Gly Glu Phe His
85 90 95

Gln Lys Gly Thr Val Arg Thr Lys Tyr Gly Thr Lys Gly Glu Leu Gln
100 105 110

Ser Ala Ile Lys Ser Leu His Ser Arg Asp Ile Asn Val Tyr Gly Asp
115 120 125

Val Val Ile Asn His Lys Gly Gly Ala Asp Ala Thr Glu Asp Val Thr
130 135 140

Ala Val Glu Val Asp Pro Ala Asp Arg Asn Arg Val Ile Ser Gly Glu
145 150 155 160

-continued

```
His Leu Ile Lys Ala Trp Thr His Phe His Phe Pro Gly Arg Gly Ser
                165                 170                 175

Thr Tyr Ser Asp Phe Lys Trp His Trp Tyr His Phe Asp Gly Thr Asp
            180                 185                 190

Trp Asp Glu Ser Arg Lys Leu Asn Arg Ile Tyr Lys Phe Gln Gly Lys
        195                 200                 205

Ala Trp Asp Trp Glu Val Ser Asn Glu Asn Gly Asn Tyr Asp Tyr Leu
    210                 215                 220

Met Tyr Ala Asp Ile Asp Tyr Asp His Pro Asp Val Ala Ala Glu Ile
225                 230                 235                 240

Lys Arg Trp Gly Thr Trp Tyr Ala Asn Glu Leu Gln Leu Asp Gly Phe
                245                 250                 255

Arg Leu Asp Ala Val Lys His Ile Lys Phe Ser Phe Leu Arg Asp Trp
            260                 265                 270

Val Asn His Val Arg Glu Lys Thr Gly Lys Glu Met Phe Thr Val Ala
        275                 280                 285

Glu Tyr Trp Gln Asn Asp Leu Gly Ala Leu Glu Asn Tyr Leu Asn Lys
    290                 295                 300

Thr Asn Phe Asn His Ser Val Phe Asp Val Pro Leu His Tyr Gln Phe
305                 310                 315                 320

His Ala Ala Ser Thr Gln Gly Gly Gly Tyr Asp Met Arg Lys Leu Leu
                325                 330                 335

Asn Gly Thr Val Val Ser Lys His Pro Leu Lys Ser Val Thr Phe Val
            340                 345                 350

Asp Asn His Asp Thr Gln Pro Gly Gln Ser Leu Glu Ser Thr Val Gln
        355                 360                 365

Thr Trp Phe Lys Pro Leu Ala Tyr Ala Phe Ile Leu Thr Arg Glu Ser
    370                 375                 380

Gly Tyr Pro Gln Val Phe Tyr Gly Asp Met Tyr Gly Thr Lys Gly Asp
385                 390                 395                 400

Ser Gln Arg Glu Ile Pro Ala Leu Lys His Lys Ile Glu Pro Ile Leu
                405                 410                 415

Lys Ala Arg Lys Gln Tyr Ala Tyr Gly Ala Gln His Asp Tyr Phe Asp
            420                 425                 430

His His Asp Ile Val Gly Trp Thr Arg Glu Gly Asp Ser Ser Val Ala
        435                 440                 445

Asn Ser Gly Leu Ala Ala Leu Ile Thr Asp Gly Pro Gly Gly Ala Lys
    450                 455                 460

Arg Met Tyr Val Gly Arg Gln Asn Ala Gly Glu Thr Trp His Asp Ile
465                 470                 475                 480

Thr Gly Asn Arg Ser Glu Pro Val Val Ile Asn Ser Glu Gly Trp Gly
                485                 490                 495

Glu Phe His Val Asn Gly Gly Ser Val Ser Ile Tyr Val Gln Arg
            500                 505                 510
```

( 2 ) INFORMATION FOR SEQ ID NO: 4:

( i ) SEQUENCE CHARACTERISTICS:
( A ) LENGTH: 520 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Bacillus amyloliquefaciens ( x i ) SEQUENCE DESCRIPTION: SEQ ID NO: 4:

Met Arg Gly Arg Gly Asn Met Ile Gln Lys Arg Lys Arg Thr Val Ser
1               5                   10                  15

Phe Arg Leu Val Leu Met Cys Thr Leu Leu Phe Val Ser Leu Pro Ile
            20                  25                  30

Thr Lys Thr Ser Ala Val Asn Gly Thr Leu Met Gln Tyr Phe Glu Trp
        35                  40                  45

Tyr Thr Pro Asn Asp Gly Gln His Trp Lys Arg Leu Gln Asn Asp Ala
    50                  55                  60

Glu His Leu Ser Asp Ile Gly Ile Thr Ala Val Trp Ile Pro Pro Ala
65                  70                  75                  80

Tyr Lys Gly Leu Ser Gln Ser Asp Asn Gly Tyr Gly Pro Tyr Asp Leu
                85                  90                  95

Tyr Asp Leu Gly Glu Phe Gln Gln Lys Gly Thr Val Arg Thr Lys Tyr
            100                 105                 110

Gly Thr Lys Ser Glu Leu Gln Asp Ala Ile Gly Ser Leu His Ser Arg
        115                 120                 125

Asn Val Gln Val Tyr Gly Asp Val Val Leu Asn His Lys Ala Gly Ala
    130                 135                 140

Asp Ala Thr Glu Asp Val Thr Ala Val Glu Val Asn Pro Ala Asn Arg
145                 150                 155                 160

Asn Gln Glu Thr Ser Glu Glu Tyr Gln Ile Lys Ala Trp Thr Asp Phe
                165                 170                 175

Arg Phe Pro Gly Arg Gly Asn Thr Tyr Ser Asp Phe Lys Trp His Trp
            180                 185                 190

Tyr His Phe Asp Gly Ala Asp Trp Asp Glu Ser Arg Lys Ile Ser Arg
        195                 200                 205

Ile Phe Lys Phe Arg Gly Glu Gly Lys Ala Trp Asp Trp Glu Val Ser
    210                 215                 220

Ser Glu Asn Gly Asn Tyr Asp Tyr Leu Met Tyr Ala Asp Val Asp Tyr
225                 230                 235                 240

Asp His Pro Asp Val Val Ala Glu Thr Lys Lys Trp Gly Ile Trp Tyr
                245                 250                 255

Ala Asn Glu Leu Ser Leu Asp Gly Phe Arg Ile Asp Ala Ala Lys His
            260                 265                 270

Ile Lys Phe Ser Phe Leu Arg Asp Trp Val Gln Ala Val Arg Gln Ala
        275                 280                 285

Thr Gly Lys Glu Met Phe Thr Val Ala Glu Tyr Trp Gln Asn Asn Ala
    290                 295                 300

Gly Lys Leu Glu Asn Tyr Leu Asn Lys Thr Ser Phe Asn Gln Ser Val
305                 310                 315                 320

Phe Asp Val Pro Leu His Phe Asn Leu Gln Ala Ala Ser Ser Gln Gly
                325                 330                 335

Gly Gly Tyr Asp Met Arg Arg Leu Leu Asp Gly Thr Val Val Ser Arg
            340                 345                 350

His Pro Glu Lys Ala Val Thr Phe Val Glu Asn His Asp Thr Gln Pro
        355                 360                 365

Gly Gln Ser Leu Glu Ser Thr Val Gln Thr Trp Phe Lys Pro Leu Ala
    370                 375                 380

Tyr Ala Phe Ile Leu Thr Arg Glu Ser Gly Tyr Pro Gln Val Phe Tyr
385                 390                 395                 400

Gly Asp Met Tyr Gly Thr Lys Gly Thr Ser Pro Lys Glu Ile Pro Ser
                405                 410                 415

-continued

Leu Lys Asp Asn Ile Glu Pro Ile Leu Lys Ala Arg Lys Glu Tyr Ala
420 425 430

Tyr Gly Pro Gln His Asp Tyr Ile Asp His Pro Asp Val Ile Gly Trp
435 440 445

Thr Arg Glu Gly Asp Ser Ser Ala Ala Lys Ser Gly Leu Ala Ala Leu
450 455 460

Ile Thr Asp Gly Pro Gly Gly Ser Lys Arg Met Tyr Ala Gly Leu Lys
465 470 475 480

Asn Ala Gly Glu Thr Trp Tyr Asp Ile Thr Gly Asn Arg Ser Asp Thr
485 490 495

Val Lys Ile Gly Ser Asp Gly Trp Gly Glu Phe His Val Asn Asp Gly
500 505 510

Ser Val Ser Ile Tyr Val Gln Lys
515 520

( 2 ) INFORMATION FOR SEQ ID NO: 5:

( i ) SEQUENCE CHARACTERISTICS:
( A ) LENGTH: 548 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Bacillus stearothermophilus ( x i ) SEQUENCE DESCRIPTION: SEQ ID NO: 5:

Val Leu Thr Phe His Arg Ile Ile Arg Lys Gly Trp Met Phe Leu Leu
1 5 10 15

Ala Phe Leu Leu Thr Ala Ser Leu Phe Cys Pro Thr Gly Arg His Ala
20 25 30

Lys Ala Ala Ala Pro Phe Asn Gly Thr Met Met Gln Tyr Phe Glu Trp
35 40 45

Tyr Leu Pro Asp Asp Gly Thr Leu Trp Thr Lys Val Ala Asn Glu Ala
50 55 60

Asn Asn Leu Ser Ser Leu Gly Ile Thr Ala Leu Ser Leu Pro Pro Ala
65 70 75 80

Tyr Lys Gly Thr Ser Arg Ser Asp Val Gly Tyr Gly Val Tyr Asp Leu
85 90 95

Tyr Asp Leu Gly Glu Phe Asn Gln Lys Gly Thr Val Arg Thr Lys Tyr
100 105 110

Gly Thr Lys Ala Gln Tyr Leu Gln Ala Ile Gln Ala Ala His Ala Ala
115 120 125

Gly Met Gln Val Tyr Ala Asp Val Val Phe Asp His Lys Gly Gly Ala
130 135 140

Asp Gly Thr Glu Trp Val Asp Ala Val Glu Val Asn Pro Ser Asp Arg
145 150 155 160

Asn Gln Glu Ile Ser Gly Thr Tyr Gln Ile Gln Ala Trp Thr Lys Phe
165 170 175

Asp Phe Pro Gly Arg Gly Asn Thr Tyr Ser Ser Phe Lys Trp Arg Trp
180 185 190

Tyr His Phe Asp Gly Val Asp Trp Asp Glu Ser Arg Lys Leu Ser Arg
195 200 205

Ile Tyr Lys Phe Arg Gly Ile Gly Lys Ala Trp Asp Trp Glu Val Asp
210 215 220

Thr Glu Asn Gly Asn Tyr Asp Tyr Leu Met Tyr Ala Asp Leu Asp Met

-continued

```
225                 230                 235                 240

Asp His Pro Glu Val Val Thr Glu Leu Lys Asn Trp Gly Lys Trp Tyr
                245                 250                 255

Val Asn Thr Thr Asn Ile Asp Gly Phe Arg Leu Asp Gly Leu Lys His
            260                 265                 270

Ile Lys Phe Ser Phe Phe Pro Asp Trp Leu Ser Tyr Val Arg Ser Gln
        275                 280                 285

Thr Gly Lys Pro Leu Phe Thr Val Gly Glu Tyr Trp Ser Tyr Asp Ile
    290                 295                 300

Asn Lys Leu His Asn Tyr Ile Thr Lys Thr Asn Gly Thr Met Ser Leu
305                 310                 315                 320

Phe Asp Ala Pro Leu His Asn Lys Phe Tyr Thr Ala Ser Lys Ser Gly
                325                 330                 335

Gly Ala Phe Asp Met Arg Thr Leu Met Thr Asn Thr Leu Met Lys Asp
            340                 345                 350

Gln Pro Thr Leu Ala Val Thr Phe Val Asp Asn His Asp Thr Asn Pro
        355                 360                 365

Ala Lys Arg Cys Ser His Gly Arg Pro Trp Phe Lys Pro Leu Ala Tyr
    370                 375                 380

Ala Phe Ile Leu Thr Arg Gln Glu Gly Tyr Pro Cys Val Phe Tyr Gly
385                 390                 395                 400

Asp Tyr Tyr Gly Ile Pro Gln Tyr Asn Ile Pro Ser Leu Lys Ser Lys
                405                 410                 415

Ile Asp Pro Leu Leu Ile Ala Arg Arg Asp Tyr Ala Tyr Gly Thr Gln
            420                 425                 430

His Asp Tyr Leu Asp His Ser Asp Ile Ile Gly Trp Thr Arg Glu Gly
        435                 440                 445

Val Thr Glu Lys Pro Gly Ser Gly Leu Ala Ala Leu Ile Thr Asp Gly
    450                 455                 460

Ala Gly Arg Ser Lys Trp Met Tyr Val Gly Lys Gln His Ala Gly Lys
465                 470                 475                 480

Val Phe Tyr Asp Leu Thr Gly Asn Arg Ser Asp Thr Val Thr Ile Asn
                485                 490                 495

Ser Asp Gly Trp Gly Glu Phe Lys Val Asn Gly Gly Ser Val Ser Val
            500                 505                 510

Trp Val Pro Arg Lys Thr Thr Val Ser Thr Ile Ala Arg Pro Ile Thr
        515                 520                 525

Thr Arg Pro Trp Thr Gly Glu Phe Val Arg Trp His Glu Pro Arg Leu
    530                 535                 540

Val Ala Trp Pro
545
```